United States Patent [19]

Vaara

[11] Patent Number: 4,510,132
[45] Date of Patent: Apr. 9, 1985

[54] COMPOUNDS FOR USE IN ANTIBACTERIAL THERAPY

[76] Inventor: Martti Vaara, A. Kannistontie 10, Helsinki, SF-00320, Finland

[21] Appl. No.: 534,617

[22] Filed: Sep. 22, 1983

[30] Foreign Application Priority Data

Oct. 6, 1982 [GB] United Kingdom ............... 8228545

[51] Int. Cl.³ ..................... A61K 37/00; C07C 103/52
[52] U.S. Cl. ................................ 514/11; 260/112.5 R
[58] Field of Search ................. 260/112.5 R; 424/177

[56] References Cited

U.S. PATENT DOCUMENTS

| | | | |
|---|---|---|---|
| 2,695,261 | 11/1954 | Ainsworth et al. | 260/112.5 R |
| 2,759,868 | 8/1956 | Bushby | 260/112.5 R |
| 4,237,045 | 12/1980 | Failli et al. | 260/112.5 R |
| 4,252,795 | 2/1981 | Failli et al. | 260/112.5 R |

Primary Examiner—Delbert R. Phillips
Attorney, Agent, or Firm—Webb, Burden, Robinson & Webb

[57] ABSTRACT

A compound having the general formula

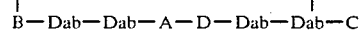

in which Dab is diaminobutyric acid; A is either leucine, threonine, isoleucine or phenylalanine; B is either leucine or threonine; D is either D-leucine or D-phenylalanine; and C is a substituent selected from the group comprising —Dab—Thr, —Dab—Thr—Dab, —Dab, —Dab—Thr—Acyl and H, in which Thr is threonine, Acyl is a lower acyl group of 1 to 5 carbon atoms and Dab is as defined above. These compounds are useful in sensitizing Gram-negative bacteria to antibacterial agents and to the host defence mechanism complement when subjecting said Gram-negative bacteria to the action of said compounds. The invention also provides a pharmaceutical composition for use in sensitizing Gram-negative bacteria to antibacterial agents, complement or both, comprising a therapeutically effective amount of said compound in admixture with a pharmaceutically acceptable carrier. Polymyxin B nonapeptide having the formula:

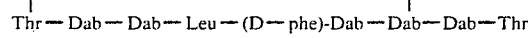

is produced by treating polymyxin B with ficin, papain or bromelin.

9 Claims, 1 Drawing Figure

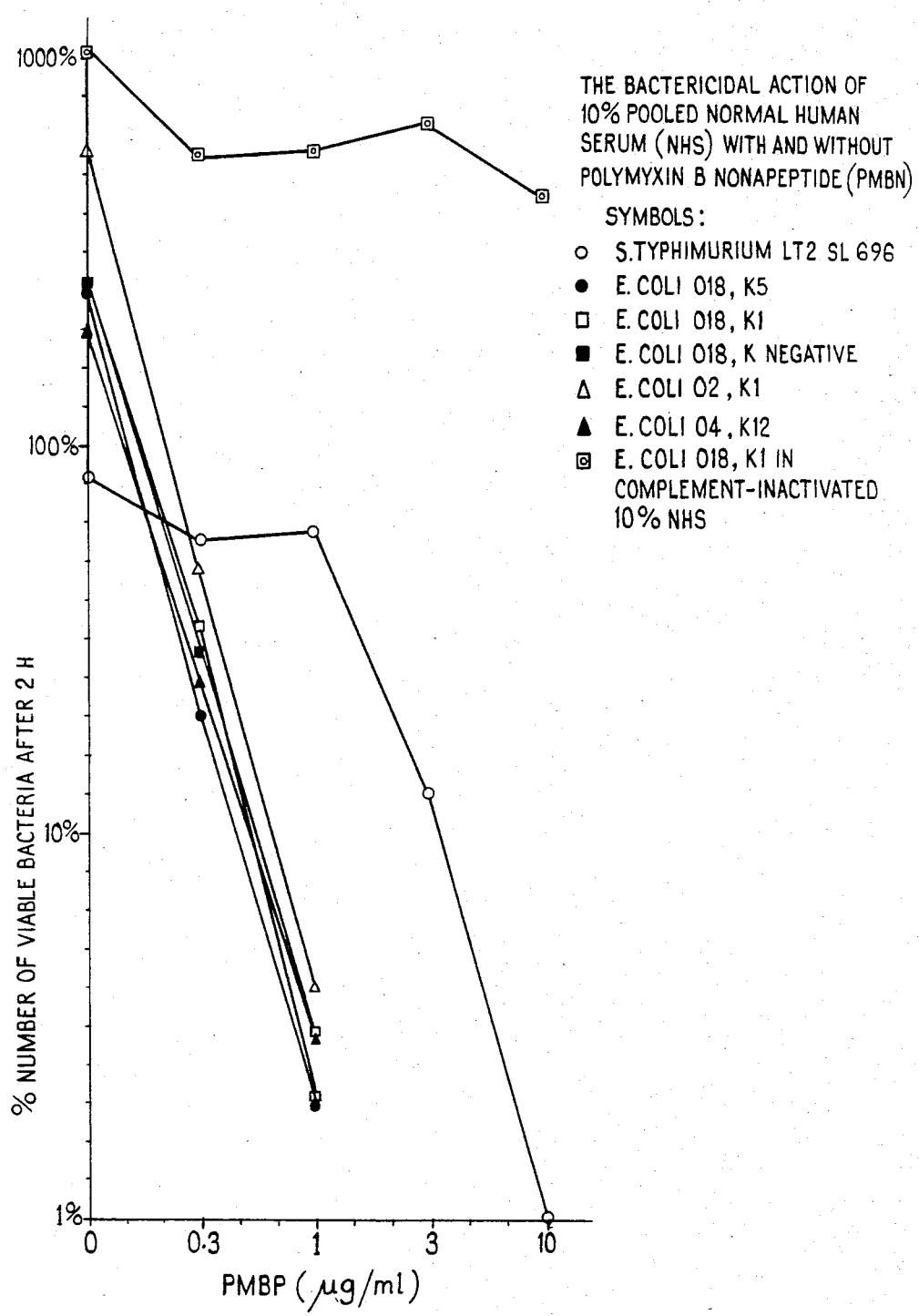

COMPOUNDS FOR USE IN ANTIBACTERIAL THERAPY

BACKGROUND OF THE INVENTION

The present invention relates to novel polymyxin, circulin and octapeptin derivatives and pharmaceutically acceptable salts thereof and their use in therapy to sensitize Gram-negative bacteria to antibacterial agents and/or to the host (human, animal) defence mechanism complement. The present invention also relates to a method of sensitizing Gram-negative bacteria to antibacterial agents and to host defence mechanism complement and to a pharmaceutical composition for use in this method. Finally the present invention relates to a method of producing a polymyxin B nonapeptide which also is a novel compound.

One reason for the resistance of bacteria to antibiotics is their cell wall which inhibit the free permeation of antibiotics to their targets inside the cell. Especially evident this is in Gram-negative bacteria which have a unique structure as their outermost barrier to external noxious agents. This special structure is an additional membrane located outside the peptidoglycan and called the outer membrane (OM). The OM of Gram-negative enteric bacteria and Pseudomonas act as an absolute permeability barrier to many antibiotics (e.g. erythromycin, lincomycin, clindamycin, novobiocin, cloxacillin, nafcillin and fusidic acid). The penetration of several other antibiotics (especially penicillin, ampicillin, carbenicillin and most cephalosporins) is also greatly reduced by the OM.

In addition to the antibiotics, the defence mechanisms of the host, such as complement, often synergistic with antibodies, and phagocytosis play a significant role in the inhibition of invading micro-organisms. Unfortunately, Gram-negative bacteria isolated from severe infections, e.g. septicemia, usually show a uniform resistance to complement. They are also poorly phagocytosed, partly because of the mentioned resistance to complement. Interestingly, also the resistance to complement has been attributed to the outer membrane.

Thus, the outer membrane is responsible not only for the resistance of Gram-negative bacteria to many antibiotics, but also for their resistance to the major host defence mechanism complement. Concomitantly, if one could affect the outer membrane structure so that it either loses its function as a permeability barrier to antibiotics or loses its resistance to complement, infections caused by Gram-negative bacteria would be much easier to control. The object of the present invention is to provide a method to affect the outer membrane structure in such a way.

SUMMARY OF THE INVENTION

According to the present invention there is now provided a novel class of compounds having a heptapeptide ring configuration of at least 4 basic diaminobutyric acid residues in addition to leucine, isoleucine, phenylalanine and threonine. Especially preferred are compounds having the general formula

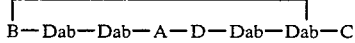

in which Dab is diaminobutyric acid; A is either leucine, threonine, isoleucine or phenylalanine; B is either leucine or threonine; D is either D-leucine or D-phenylalanine; and C is a substituent selected from the group comprising —Dab—Thr, —Dab—Thr—Dab, —Dab, —Dab—Thr—Acyl, and H, in which Thr is threonine, Acyl is a lower acyl group of 1 to 5 carbon atoms, and Dab is as defined above. Illustrative examples of compounds within the above general formula are polymyxin B nonapeptide, and octapeptin heptapeptide. Within this broad class of compounds there are some compounds which are prior known and therefore excluded from the broad definition given above. Such are polymyxin E nonapeptide (colistin nonapeptide), deacylpolymyxin B and E, deacyloctapeptin, polymyxin B heptapeptide, polymyxin E heptapeptide, and polymyxin M heptapeptide (Jap 4178/1971; Kurihara et al, Yakugaku Zasshi 94,1491, 1974; Srinivasa et al, Indian J. Biochem. Biophys. 17,298, 1980; Parker and Rathnum, J. Antibiot. 28,379, 1975; Suzuki et al, J. Biochem. Japan 56,335, 1964; Ger 2.038.997/1971; Engl. 1.323.362/1973; Salem et al, Zh. Obshch.Khim. 68,38, 1968).

The present invention also provides a method of sensitizing Gram-negative bacteria to antibacterial agents and to the host defence system complement by subjecting said Gram-negative bacteria to the action of a compound having the above general formula. Although some of the compounds included in the above general formula are prior known, e.g. polymyxin E nonapeptide (colistin nonapeptide), deacylpolymyxin B and E, deacyloctapeptin, polymyxin B heptapeptide, polymyxin E heptapeptide, and polymyxin M heptapeptide (Jap 4178/1971; Kurihara et al, Yakugaku Zasshi 94,1491, 1974; Srinivasa et al, Indian J. Biochem. Biophys. 17,298, 1980; Parker and Rathnum, J. Antibiot. 28,379, 1975; Suzuki et al, J. Biochem. Japan 56,335, 1964; Ger 2.038.997/1971; Engl. 1.323.362/1973; Salem et al, Zh. Obshch.Khim. 68,38, 1968), the sensitizing effect thereof to antibiotics and complement has not been thus far studied and no therapeutical use has thus far been described for them or for other compounds within the broad definition given above. For instance Chihara et al and Kajiwara et al showed that polymyxin E nonapeptide (colistin nonapeptide) is significantly less toxic to eukaryotes (mice) than its parent compound, colistin, but it was also shown to lack the antibacterial activity of colistin (Chihara et al, Agr.Biol.Chem. 37,2455, 1973 and 38,521, 1974). Its sensitizing effect to antibiotics and complement was not studied and no therapeutical use has thus far been described for it.

PREPARATION OF THE COMPOUNDS

The compounds include in the present invention as defined in the general formula above may be prepared analogously with the methods already known. The nonapeptide compounds could be prepared for instance by treating polymyxins or circulins with enzymes such as ficin, papain, or bromelin. The deacyl compounds could be prepared for instance by treating polymyxins, circulins or octapeptin with for instance hydrazine or acids like formic acid or oxalic acid. The heptapeptide derivatives of polymyxins or circulins could be prepared by proteolytic enzymes such as subtilopeptidase.

Deacylpolymyxin E may be prepared by deacylating polymyxin E for example by the method of Kurihara et al. (Yakugaku Zasshi, 94, 1941, 1974). Colistin (polymyxin E) sulfate, 2.0 g, is dissolved into 50 ml of deionized water and the pH of the solution is adjusted to pH 11 with 1N NaOH. The precipitate (colistin base) is washed with water and dissolved in 6N formic acid. The solution is incubated for 7 hours at 70° C. whereafter the reaction mixture is steam distilled, the residual liquor is condensed under reduced pressure, and the residue is lyophilized. The material is subsequently subjected to gel filtration in a Sephadex-G10 column and the ninhydrin positive fractions are collected and analyzed in thin layer chromatography (cellulose plates; solvent n-butanol-acetic acid-water, 4/1/2 by vol., ninhydrin staining). The fraction with an Rf-value of approx. 0.15 represents deacylpolymyxin E.

Polymyxin E heptapeptide again may be prepared by enzymatic hydrorolysis of polymyxin E by using for example the method described in the Japanese patent specification No. 99197/1980. 2 g of colistin (=polymyxin E) sulfate is dissolved in deionized water and 200 mg of colistin hydrolase is added. The solution is adjusted to 0.01M and pH 9.0 with 0.1M borate buffer and incubated at 37° C. for 3 hours. THe solution is adjusted to pH 4.0 and adsorbed on 500 ml of IRC-50 (H+ form) column. The elution is done with HCl-methanol-water (5/45/50, by vol; 15 ml fractions). The fractions are analyzed in paper chromatography (solvent: n-butanol-acetic acid-water; 4/1/2 by vol.) and the fractions having a ninhydrine-positive compound with an Rf-value of 0.76 were pooled. Methanol is removed under reduced pressure. The residue is adjusted to near pH 5 with a strong base resin (IRA-410), and then to near pH 7.2 with a strong base resin (IRA-410), and then to near pH 7.2 with dilute NaOH to precipitate polymyxin E heptapeptide base.

Alternatively, subtilisin A (EC 3.4.4.16, e.g. from Sigma Chemical Co., St. Louis, MO) can be used instead of colistin hydrolase, because also this enzyme hydrolyzes polymyxins to their heptapeptides (Suzuki et al., J. Biochem. 56, 335, 1964.

DESCRIPTION OF THE PREFERRED EMBODIMENTS

To sensitize Gram-negative bacteria to antibacterial agents or to complement, bacteria are incubated with a particular antimicrobial agent or complement source in the presence of at least some of the compounds having the above general formula.

As a contrast to native polymyxins and octapeptins, those derivatives have a significantly reduced or lacking direct antibacterial activity. It has, however, now been found that e.g. the derivative of polymyxin B lacking both the fatty acid part and the terminal diaminobutyric acid and named polymyxin B nonapeptide (PMBN), sensitizes at cconcentrations of 1-3 μg/ml both Salmonella and E. coli to most of the tested antibiotics by a factor of 10-30. Already 0.3 μg of PMBN is sufficient to sensitize E. coli to erythromycin and fusidic acid by a factor of 30.

It has now also been found that PMBN sensitizes bacterial strains to the bactericidal action of normal human serum (NHS). The E. coli strains tested were resistant to 10% NHS in the absence of PMBN but already 0.3 μg/ml of PMBN sensitized them to 10% NHS. Three μg/ml of PMBN was required to sensitize Salmonella to 10% NHS. When the complement in NHS was destroyed by heat (30 min at 56° C.) or zymosan A-treatment, NHS lost its bactericidal, PMBN-dependent action, indicating that PMBN acts synergistically with complement.

It has now also been demonstrated that a combination of polymyxin B nonapeptide with antibiotics such as erythromycin or clindamycin, as an example, protects mice infected with virulent bacteria (E. coli) from death while the used doses of erythromycin or clindamycin alone, without polymyxin B nonapeptide were not protective.

It has now also been demonstrated that an analogous derivative of polymyxin E (polymyxin E derivative lacking the fatty acid part and the terminal diaminobutyric acid, polymyxin E nonapeptide, colistin nonapeptide) has a similar action as polymyxin B nonapeptide.

The present invention is disclosed in more detail by way of the following examples.

EXAMPLE 1

Preparation of polymyxin B nonapeptide (PMBN) using ficin

Polymyxin B nonapeptide was prepared by an enzymatic ficin treatment of polymyxin B analogously with a method originally developed by Kajiwara et al (Japanese patent specification No. 4178/1971) for preparing colistin nonapeptide from colistin (=polymyxin E).

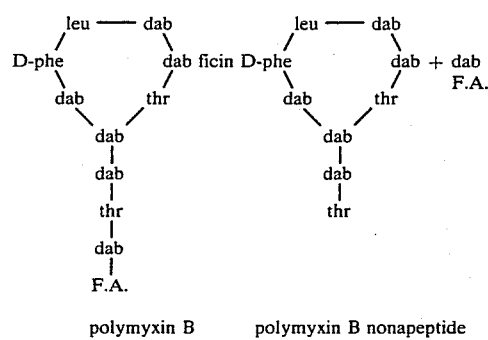

abbreviations:
dab = diaminobutyric acid
phe = phenylalanine
thr = threonine
F.A. = fatty acyl group Treatment with ficin. 52 mg of polymyxin B sulfate (Sigma Chemical Co., St. Louis, Mo., United States; corresponding to approx. 37 mg of polymyxin B) was dissolved in 4 ml of 0.07M potassium phosphate buffer pH 7.2, whereafter 1 ml of ficin suspension (EC 3.4.22.3, Sigma Chemical Co. P-4125, containing 25 mg of protein) was added and the mixture incubated at 37° C. for 36 h with light shaking. The mixture was then stirred in boiling water for 5 min and the formed precipitate (denatured ficin) was removed.

Purification of polymyxin B nonapeptide. The solution was adjusted to pH 2 with 1N HCl and washed twice with 2.5 ml of n-butanol, then to pH 9 with 1N NaOH and again washed twice with 2.5 ml of n-butanol. 2.6 ml of the solution was then mixed with 44 ml of CM-Sephadex C 50 suspension (Pharmacia Fine Chemicals AB, Uppsala, Sweden, 0.25 g/100 ml of deionized water), incubated at 37° C. for 5 min with shaking, centrifuged (1000 g, 10 min) and washed with 20 ml of deionized water. Polymyxin B nonapeptide was eluted from the Sephadex beads by 2×20 ml of 10% pyridine—10% acetic acid in water, lyophilized, dissolved in deionized water and stored at −20° C.

Yield and purity. Polymyxin B nonapeptide concentration was calculated from the amount of free amino groups found in amino-group determination using a molecular weight of 950d. Polymyxin B sulfate was used as a control. The yield was 63%. The aqueous solution of polymyxin B nonapeptide preparation 1 mg/ml was neutral (pH 7).

For purity analysis, the preparation was run in TLC using cellulose coated aluminum foils (E. Merck, Darmstadt, West Germany) and the solvent system n-butanol-pyridine-acetic acid-water (30:20:6:24; per volume). The spots were visualized by ninhydrin. The Rf-value for polymyxin B was 0.56, for polymyxin B nonapeptide 0.48 and for fatty acyl diaminobutyric acid (formed in the enzymatic treatment) 0.77. TLC of the polymyxin B nonapeptide preparation (maximal sample used was 20 μg) revealed only the spot with Rf-value of 0.48 whereas 0.05 μg of polymyxin B still gave a visible spot with Rf-value of 0.56. When 0.1 μg of polymyxin B sulfate was mixed with 10 μg of polymyxin B nonapeptide preparation is still migrated separately (Rf-value 0.56) from polymyxin B nonapeptide.

EXAMPLE 2

Preparation of polymyxin B nonapeptide (PMBN) using papain 4 g of polymyxin B sulfate (Sigma Chemical Company, St. Louis, Mo., United States; corresponding to approx. 2.9 g of polymyxin B) was dissolved in 80 ml of deionized water. 589 mg of papain (papainase, EC 3.4.22.2, Sigma type III, P-4762, 21 U/mg) was dissolved in 10 ml of deionized water. The solutions were combined, 5 drops of toluene was added, and the mixture was incubated for 48 h at 37° C. under rotary shaking (220 rpm). The mixture was then stirred in boiling water for 5 min and the formed precipitate (denatured papain) was removed by centrifugation and filtration through Millipore filter ($\phi$0.45 um).

The solution was adjusted to pH 2 with 1N HCl and washed twice with 40 ml of n-butanol, then to pH 9 with 1N HCl, again washed twice with n-butanol, and neutralized (pH 7). The solution was then run through Amberlite IRA-410 column (OH-form, volume 50 ml) using 0.05M pyridine (adjusted to pH 7.0 with acetic acid) as eluent, concentrated, desalted in Sephadex G-10 column (volume 48 ml), and lyophilized.

Purity analysis gave the same results as in Example 1.

EXAMPLE 3

Sensitization of *Salmonella typhimurium* to antibiotics by polymyxin B nonapeptide (PMBN)

Methods. Smooth *Salmonella typhimurium* LT2 strain SL 696 (Wilkinson et al 1972 J. Gen. Microbiol. 70,527) was used as indicator organism. It was grown in Luria broth (Miller 1972. Experience in molecular genetics, Cold Spring Harbor Laboratory, New York) at 37° C. in a rotary shaker (220 rpm) into early logarithmic growth phase (Klett 40 units, Klett-Summerson colorimeter, red filter) washed with 0.9% NaCl and resuspended in 0.9% NaCl (final optical density 120 Klett units corresponding to approx. $10^9$ cells/ml).

The following antibiotics were used: novobiocin (Sigma Chemical Co., St. Louis, Mo., United States), fusidic acid (sodium salt; Løvens Kemiske Fabrik, Copenhagen, Denmark), erythromycin ethylsuccinate (Orion Pharmaceuticals, Helsinki, Finland), clindamycin hydrochloride (The Upjohn Company, Kalamazoo, Mich., United States), nafcillin (sodium salt; Wyeth, Great Valley, Philadelphia, Pa., United States), cloxacillin (sodim salt; Astra, Södertälje, Sweden), and benzylpenicillin (sodium Salt; Novo Industri, Copenhagen, Denmark). Erythromycin ethylsuccinate stock solution was prepared by dissolving 5.5 mg of erythromycin ethylestolate with 2 ml of 96% ethanol whereafter deionized water was added to a final volume of 5.5 ml. Other antibiotics were readily dissolved in deionized water.

Experimental procedure: Davis minimal growth medium (Sanderson et al, 1972, Bact. Rev. 36,608) containing glucose (1 g/l), casaminoacids (1 g/l. Difco), tryptophan (20 mg/l), and increasing amounts of a particular antibiotic was inoculated with $10^4$ cells per ml of a fresh suspension of indicator bacteria. Aliquots (200 μl) of this inoculated medium were pipetted in wells of a microtiter plate (Titertek, CAT NO. 76-213-05, Flow Laboratories, United States). Each well already contained increasing amounts of the particular polycationic agent in 30 μl of 0.9% NaCl. The plates were sealed with adhesive tape and incubated at 37° C. for 18 h. The lowest concentration of the antibiotic that completely inhibited visible growth was recorded.

Results. The results are presented in Table 1.

TABLE 1

The effect of polymyxin B nonapeptide (PMBN) on the minimum inhibitory concentration (MIC) of various antibiotics. Each value represent the MIC of a particular antibiotic in the presence of indicated concn of PMBN.

| | the concn of PMBN (μg/ml) | | | | | |
|---|---|---|---|---|---|---|
| | 0 | 0.3 | 1 | 3 | 10 | 30 |
| Novobiocin | ≧100 | 10 | 3 | 3 | 1 | 1 |
| Fusidic acid | 300 | 100 | 30 | 30 | 10 | ≧3 |
| Erythromycin | ≧100 | 30 | 10 | 10 | 3 | 3 |
| Clindamycin | 100 | 30 | 10 | 10 | 10 | 10 |
| Cloxacillin | ≧1000 | 300 | 100 | 100 | 30 | 30 |
| Nafcillin | ≧1000 | ≧1000 | 100 | 100 | 30 | 30 |
| Benzylpenicillin | 10 | 10 | 10 | 3 | 3 | 1 |

Conclusions. PMBN sensitized *Salmonella typhimurium* strain SL 696.
≧100 times to novobiocin
≧100 times to fusidic acid
≧30 times to cloxacillin
≧30 times to nafcillin
≧30 times to erythromycin
10 times to clindamycin
10 times to benzylpenicillin
The concentrations of PMBN required to sensitize the bacteria to most antibiotics by a factor of 10–30 was 1–3 μg/ml.

EXAMPLE 4

Sensitization of *E. coli* to antibiotics by polymyxin B nonapeptide (PMBN)

Methods. The methods were those presented in Example 3 except that *E. coli* was used as the test organism. The *E. coli* strain was IH 3080 (018:K1) isolated from the cerebrospinal fluid of a neonate with meningitis.

Results: The results are presented in Table 2.

TABLE 2

The effect of PMBN on the MIC of various antibiotics. Each value represent the MIC of a particular antibiotic in the presence of indicated concn of PMBN.

| | [PMBN] (μg ml$^{-1}$) | | | | |
|---|---|---|---|---|---|
| | 0 | 0.3 | 1 | 3 | 10 |
| Erythromycin | 30 | 1 | 1 | 1 | 1 |
| Clindamycin | 30 | 3 | 3 | 3 | 3 |
| Rifampicin | 3 | 3 | 0.1 | 0.03 | 0.03 |

TABLE 2-continued

The effect of PMBN on the MIC of various antibiotics. Each value represent the MIC of a particular antibiotic in the presence of indicated concn of PMBN.

| | [PMBN] ($\mu g\ ml^{-1}$) | | | | |
|---|---|---|---|---|---|
| | 0 | 0.3 | 1 | 3 | 10 |
| Fusidic acid | 100 | 3 | 3 | 3 | 1 |
| Novobiocin | 30 | 10 | 10 | 3 | 3 |
| Cloxacillin | >300 | 100 | 100 | 30 | 30 |
| Benzylpenicillin | 10 | 10 | 10 | 3 | 3 |

Conclusions. PMBN sensitized *E. coli* 018:K1 strain IH 3080.
100 times to rifampicin
100 times to fusidic acid
100 times to cloxacillin
$\geq$100 times to erythromycin
10 times to novobiocin
10 times to clindamycin
3 times to benzylpenicillin The concentrations of PMBN required to sensitize the bacteria to most antibiotics by a factor of 10–30 was 0.3–1.0 $\mu$g/ml.

EXAMPLE 5

Sensitization of enteric bacteria of normal human serum by polymyxin B nonapeptide (PMBN)

Methods. The strains used were smooth *Salmonella typhirmurium* LT2 strain SL 696 (Wilkinson et al 1972 J. Gen. Microbiol. 70, 527) and the following *E. coli* strains isolated at the National Public Health Institute, Helsinki: IHE 3080 (018,K1), EH 817 (018,K1− derivative of IHE 3080), IHE 11038 (018,K5), IHE 11055 (02,K1), and IHE 11167 (04,K12). Bacteria were grown in Luria broth (Miller 1972. Experiments in molecular genetics, Cold Spring Harbor Laboratory, New York) at 37° C. in a rotary shaker (220 rpm) into early logaritmic growth phase (Klett 40 units, Klett-Summerson colorimeter, red filter) washed with PBS (phosphate buffered saline, 8.0 g of NaCl, 0.2 g of KCl, 1.44 g of $Na_2HPO_4 x2H_2O$ and 0.2 g of $KH_2PO_4$ per liter) and resuspended in PBS, (final optical density 120 Klett units corresponding to approx. $10^9$ cells/ml).

Pooled normal human serum from 39 healthy blood donors was used as complement source. It was stored at −70° C. before use. To inactive the complement, serum was incubated at 56° C. for 30 min, or treated with zymosan A (Sigma Chemical Co., 20 mg/ml) for 1 hour at 37° C. and centrifuged.

Experimental procedure: 10% NHS in PBS was inoculated with approx. 300 cells of freshly grown bacteria and pipetted in 200 $\mu$l aliquots in wells of mictrotiter plate (Titertek ®, CAT NO. 76-213-05). The wells already contained increasing amounts of PMBN in 30 $\mu$l of 0.9% NaCl. The plate was incubated at 37° C. for 2 h whereafter each well was emptied onto Luria-agar plates. The agar plates were incubated overnight at 37° C. and the developed colonies were counted.

Results and conclusions. The results are illustrated in FIG. 1. 10% NHS did not alone (without PMBN) kill any of the six bacterial strains tested but even promoted the growth of five strains. Already 0.3 $\mu$g/ml of PMBN sensitized the *E. coli* strains to the killing by 10% NHS. To sensitize Salmonella, 3 $\mu$g/ml of PMBN was required.

If the complement in the serum was inactivated by heating or by zymosan, the serum lost its capacity to kill bacteria in the presence of PMBN. This indicates that PMBN sensitizes the bacteria to the killing action of serum complement.

EXAMPLE 6

The therapeutic effect of polymyxin B nonapeptide (PMBN) combined with erythromycin in experimental infection in mice Methods. *E. coli* strain IH 3080 (018:K1) was grown into logarithmic growth phase in Luria broth. The bacteria were injected intraperitoneally in female NMRI mice (weight 25–30 g., $3.8 \times 10^7$ bacteria/kg). Three hours after this infection, one group of mice were given a single injection of PMBN (10 mg/kg) subcutaneously. Four hours after the infection, all mice were given a single injection of erythromycin (10 mg/kg) intraperitoneally. The mice were followed 7 days for deaths.

Results. The results are presented in Table 3.

TABLE 3

The lethality of *E. coli* infection in mice given erythromycin (control group) or erythromycin plus PMBN (PMBN-group).

| | Number of mice | Number of dead mice days after infection | | | | | | |
|---|---|---|---|---|---|---|---|---|
| | | 1 | 2 | 3 | 4 | 5 | 6 | 7 |
| Control group (erythromycin) | 10 | 7 | 8 | 9 | 9 | 9 | 9 | 9 |
| PMBN-group (erythromycin plus PMBN) | 10 | 0 | 0 | 0 | 0 | 0 | 0 | 0 |

Conclusions. Erythromycin alone was without any therapeutic action against the *E. coli* infection but a combination of erythromycin and PMBN was very effective.

EXAMPLE 7

The therapeutic effect of PMBN combined with clindamycin in experimental infection in mice Methods. *E. coli* strain IH 3080 (018:K1) was grown into logarithmic growth phase in Luria broth. The bacteria were injected intraperitoneally in female NMRI mice (weight 25–30 g., $5.0 \times 10^7$ bacteria/kg). Three hours after this infection, one group of mice were given a single injection of PMBN (5 mg/kg) intraperitoneally. Four hours after the infection, all mice were given a single injection of clindamycin (100 mg/kg). The mice were followed 5 days for deaths.

Results. The results are presented in Table 4.

TABLE 4

The lethality of *E. coli* infection in mice given clindamycin (control group) or clindamycin plus PMBN (PMBN-group).

| | Number of mice | Number of dead mice days after infection | | | | |
|---|---|---|---|---|---|---|
| | | 1 | 2 | 3 | 4 | 5 |
| Control group (clindamycin) | 14 | 1 | 11 | 12 | 12 | 12 |
| PMBN-group (clindamycin plus PMBN) | 16 | 0 | 1 | 1 | 1 | 1 |

Conclusions. Clindamycin alone was without any therapeutic action against the *E. coli* infection in the conditions used but a combination of clindamycin and PMBN was very effective.

EXAMPLE 8

Sensitization of *E. coli* and *Salmonella typhimurium* to antibiotics (fusidic acid) by polymyxin E nonapeptide (PMEN).

Methods. The known compound, polymyxin E nonapeptide (colistin E nonapeptide, Japanese patent specification Nos. 4178/1971 and 51355/1972) having the following formula:

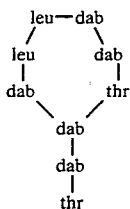

where leu is leucine, thr is threonine, and dab is diaminobutyric acid, was prepared from polymyxin E (colistin) using an enzymatic ficin treatment as described by Chihara et al (Agr. Biol. Chem. 37,2455, 1973). The bacterial strains and the method used in the sensitivity determination has been described in Example 3 and 4.

Results. The results are given in Table 5.

TABLE 5

The effect of polymyxin E nonapeptide (PMEN) on the minimum inhibitory concentration (MIC) of fusidic acid against *E. coli* and *S. typhimurium*. Each value represent the MIC of fusidic acid in presence of indicated concn of PMEN

| | The concn of PMEN ($\mu$g/ml) | | | | | |
|---|---|---|---|---|---|---|
| | 0 | 0.3 | 1.0 | 3.0 | 10 | 30 |
| E. coli | 100 | 10 | 10 | 3 | 3 | 1 |
| S. typhimurium | 300 | 100 | 30 | 10 | 3 | 1 |

What is claimed is:

1. A compound having the general formula

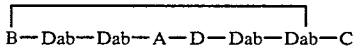

in which Dab is diaminobutyric acid; A is selected from a group comprising leucine, iso-leucine and phenylalanine; B is selected from a group comprising leucine and threonine; D is selected from a group comprising D-leucine and D-phenylalanine; and C is a substituent selected from the group comprising —Dab—Thr, —Dab—Thr—Dab, —Dab, —Dab—Thr—Acyl and H, in which Thr is threonine and Dab is as defined above the Acyl is a lower acyl group of 1 to 5 carbon atoms provided that
   when A is leucine, B is threonine and D is D-leucine, then C representing —Dab—Thr is excluded;
   when A is leucine and B is threonine, then C representing H or —Dab—Thr—Dab is excluded.

2. The compound of claim 1, wherein A is leucine, B is threonine, D is D-phenylalanine, and C is —Dab—Thr.

3. The compound of claim 1, wherein A is leucine or phenylalanine, B is leucine, D is D-leucine or phenylalanine, and C is H.

4. The compound of claim 1 wherein A is leucine, B is threonine, D is D-phenylalanine and C is the group —Dab—Thr—Acyl, wherein Acyl is a lower acyl group of 1 to 5 carbon atoms.

5. A method of sensitizing Gram-negative bacteria to antibacterial agents and to the host defence mechanism complement, comprising subjecting said Gram-negative bacteria to the action of a compound having the general formula

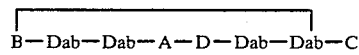

in which Dab is diaminoburyric acid; A is selected from a group comprising leucine, threonine, isoleucine and phenylalanine; B is selected from a group comprising leucine and threonine; D is selected from a group comprising D-leucine and D-phenylalanine; and C is a substituent selected from the group comprising —Dab—Thr, —Dab—Thr—Dab, —Dab, —Dab—Thr—Acyl and H, in which Thr is threonine, Acyl is a lower acyl group of 1 to 5 carbon atoms and Dab is as defined above.

6. The method of claim 5, comprising subjecting said Gram-negative bacteria to the action of at least one compound selected from the group comprising: polymyxin B nonapeptide, circulin A nonapeptide, polymyxin E nonapeptide, octapeptin heptapeptide, deacylpolymyxin B, deacylpolymyxin E, polymyxin E heptapeptide, polymyxin B heptapeptide, acylated polymyxin B nonapeptide and deacyloctapeptin.

7. A pharmaceutical composition for use in sensitizing Gram-negative bacteria to antibacterial agents, complement or both, comprising a therapeutically effective amount of a compound having the general formula

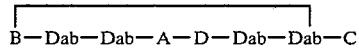

in which Dab is diaminobutyric acid; A is selected from a group comprising leucine, threonine, isoleucine and phenylalanine; B is selected from the group comprising leucine and threonine; D is selected from a group comprising D-leucine and D-phenylalanine; and C is a substituent selected from the group comprising —Dab—Thr, —Dab—Thr—Dab, —Dab, —Dab—Thr—Acyl and H, in which Thr is threonine, Acyl is a lower acyl group of 1 to 5 carbon atoms and Dab is as defined above, or an acid addition salt thereof with a pharmaceutically acceptable acid; in admixture with a pharmaceutically acceptable carrier.

8. Acid addition salts with a pharmaceutically acceptable acid of a compound as claimed in claim 1.

9. A compound as claimed in claim 1 or an acid addition salt thereof with a pharmaceutically acceptable acid for use in therapy.

* * * * *